(12) United States Patent
O'Connell et al.

(10) Patent No.: US 8,961,791 B2
(45) Date of Patent: Feb. 24, 2015

(54) MOLECULAR EXCHANGE DEVICE

(75) Inventors: Mark Thomas O'Connell, Huntingdon (GB); Stewart Jeffrey Block, London (GB); Rodney Ruston, Milton Keynes (GB)

(73) Assignee: Probe Scientific Limited, Coventry (GB)

( * ) Notice: Subject to any disclaimer, the term of this patent is extended or adjusted under 35 U.S.C. 154(b) by 610 days.

(21) Appl. No.: 12/867,458

(22) PCT Filed: Feb. 5, 2009

(86) PCT No.: PCT/GB2009/000321
§ 371 (c)(1),
(2), (4) Date: Nov. 8, 2010

(87) PCT Pub. No.: WO2009/101386
PCT Pub. Date: Aug. 20, 2009

(65) Prior Publication Data
US 2011/0049040 A1    Mar. 3, 2011

(30) Foreign Application Priority Data
Feb. 13, 2008    (GB) .................................. 0802667.6

(51) Int. Cl.
*B01D 29/54* (2006.01)
*A61M 25/00* (2006.01)
(Continued)

(52) U.S. Cl.
CPC ............ *A61M 25/00* (2013.01); *A61B 5/14528* (2013.01); *A61B 5/0075* (2013.01); *A61B 5/0084* (2013.01); *A61B 5/14503* (2013.01)
USPC .................. 210/338; 210/321.78; 210/321.87; 210/323.2; 210/645; 210/437; 422/535; 604/6.16

(58) Field of Classification Search
CPC ............ A61M 25/00; A61M 25/0021; A61M 25/0023; A61M 25/0041; A61M 25/0043; A61M 25/005; A61M 25/0051; A61M 25/0052; A61M 25/0053; A61M 25/008; A61M 2025/00; A61M 2025/0042; A61M 2025/0059; A61B 5/14525; A61B 5/14528; A61B 5/15; A61B 5/4839
USPC ............................................. 210/437, 497.01
See application file for complete search history.

(56) References Cited

U.S. PATENT DOCUMENTS 3,670,772 A * 6/1972 Ziemek et al. ................. 138/114
3,981,299 A * 9/1976 Murray ........................... 604/43
(Continued)

FOREIGN PATENT DOCUMENTS

EP    0381062 A2    8/1990
EP    0558071 A     9/1993
(Continued)

OTHER PUBLICATIONS

United Kingdom Intellectual Property Office, United Kingdom Search Report for Great Britain Application No. GB0802667.6, Jun. 13, 2008, 4 pages.
(Continued)

*Primary Examiner* — David C Mellon
*Assistant Examiner* — Pranav Patel
(74) *Attorney, Agent, or Firm* — Klarquist Sparkman, LLP

(57) ABSTRACT

The present relates to a molecular exchange device. In particular, the present invention relates to a molecular exchange device comprising an outer tube extending from an approximal end to a distal end of the device; an inner tube defining at least one fluid passageway, the inner tube positioned concentrically within the outer tube and the area between the inner and the outer tube defining at least one fluid passageway; and a projection positioned within the area between the inner and the outer tube, wherein the projection prevents displacement of the inner tube with respect to the outer tube.

17 Claims, 4 Drawing Sheets

(51) Int. Cl.
*A61B 5/145* (2006.01)
*A61B 5/00* (2006.01)

(56) References Cited

U.S. PATENT DOCUMENTS

| | | | |
|---|---|---|---|
| 4,265,249 A | | 5/1981 | Schindler et al. |
| 4,274,417 A | * | 6/1981 | Delpy ............................ 600/364 |
| 4,312,757 A | * | 1/1982 | Brumfield ...................... 210/646 |
| 4,694,832 A | | 9/1987 | Ungerstedt |
| 4,707,268 A | | 11/1987 | Shah et al. |
| 4,753,221 A | * | 6/1988 | Kensey et al. .................. 600/16 |
| 5,106,365 A | | 4/1992 | Hernandez |
| 5,308,338 A | | 5/1994 | Helfrich |
| 5,441,481 A | | 8/1995 | Mishra et al. |
| 6,299,593 B1 | | 10/2001 | Wakabayashi |
| 6,346,090 B1 | | 2/2002 | Liska et al. |
| 6,478,767 B1 | | 11/2002 | O'Connell |
| 6,616,625 B2 | * | 9/2003 | Haindl ............................ 604/27 |
| 6,716,189 B1 | * | 4/2004 | Jarvik et al. .................. 604/6.16 |
| 6,805,683 B1 | | 10/2004 | Johansson |
| 6,929,618 B1 | | 8/2005 | Johansson |
| 2003/0060751 A1 | | 3/2003 | Haindl |
| 2003/0167031 A1 | * | 9/2003 | Odland ............................ 604/8 |
| 2003/0236454 A1 | | 12/2003 | Liska et al. |
| 2005/0119588 A1 | * | 6/2005 | Model et al. .................. 600/581 |
| 2005/0251087 A1 | | 11/2005 | Carr et al. |
| 2005/0277820 A1 | * | 12/2005 | Wright et al. .................. 600/366 |
| 2006/0079830 A1 | | 4/2006 | Putz |
| 2007/0095756 A1 | | 5/2007 | Hardwicke et al. |
| 2007/0197959 A1 | * | 8/2007 | Panotopoulos ............ 604/93.01 |

FOREIGN PATENT DOCUMENTS

| | | |
|---|---|---|
| EP | 0675695 B1 | 10/1995 |
| EP | 1101501 A1 | 5/2001 |
| FR | 2655548 A1 | 6/1991 |
| GB | 2030454 A | 4/1980 |
| GB | 2053719 A | 2/1981 |
| GB | 2130916 A | 6/1984 |
| JP | 61 206459 A | 9/1986 |
| WO | WO93/00128 A | 1/1993 |
| WO | WO95/10357 | 4/1995 |
| WO | WO98/46339 | 10/1998 |
| WO | WO00/10464 | 3/2000 |
| WO | WO01/03763 A | 1/2001 |
| WO | WO01/06928 A1 | 2/2001 |
| WO | WO01/19444 A1 | 3/2001 |
| WO | WO2004/033000 A1 | 4/2004 |

OTHER PUBLICATIONS

International Search Report and Written Opinion of the International Searching Authority, mailed May 7, 2009, for corresponding International Application No. PCT/GB2009/000321, 12 pages.
United Kingdom Intellectual Property Office, United Kingdom Search Report for Great Britain Application No. GB0802669.2, Jun. 13, 2008, 4 pages.
United Kingdom Intellectual Property Office, United Kingdom Search Report for Great Britain Application No. GB0619157.1, Jun. 20, 2007, 4 pages.
International Search Report and Written Opinion of the International Searching Authority, mailed May 26, 2008, for International Application No. PCT/GB2007/003695, 14 pages.
International Preliminary Report on Patentability and Written Opinion of the International Searching Authority, mailed Mar. 31, 2009, for International Application No. PCT/GB2007/003695, 9 pages.
International Search Report and Written Opinion of the International Searching Authority, mailed Dec. 8, 2010, for International Application No. PCT/GB2009/000312, 13 pages.
Office Action from the United States Patent & Trademark Office in U.S. Appl. No. 12/443,449, dated Sep. 2, 2011.
Office Action from the United States Patent & Trademark Office in co-pending U.S. Appl. No. 12/443,449, dated Mar. 12, 2012.
Office Action from the United States Patent & Trademark Office in co-pending U.S. Appl. No. 12/867,459, dated Nov. 2, 2012.
Office Action from the United States Patent & Trademark Office in co-pending U.S. Appl. No. 12/867,459, dated Mar. 5, 2013.
Office Action from the United States Patent & Trademark Office in co-pending U.S. Appl. No. 12/867,459, dated Sep. 9, 2013.

* cited by examiner

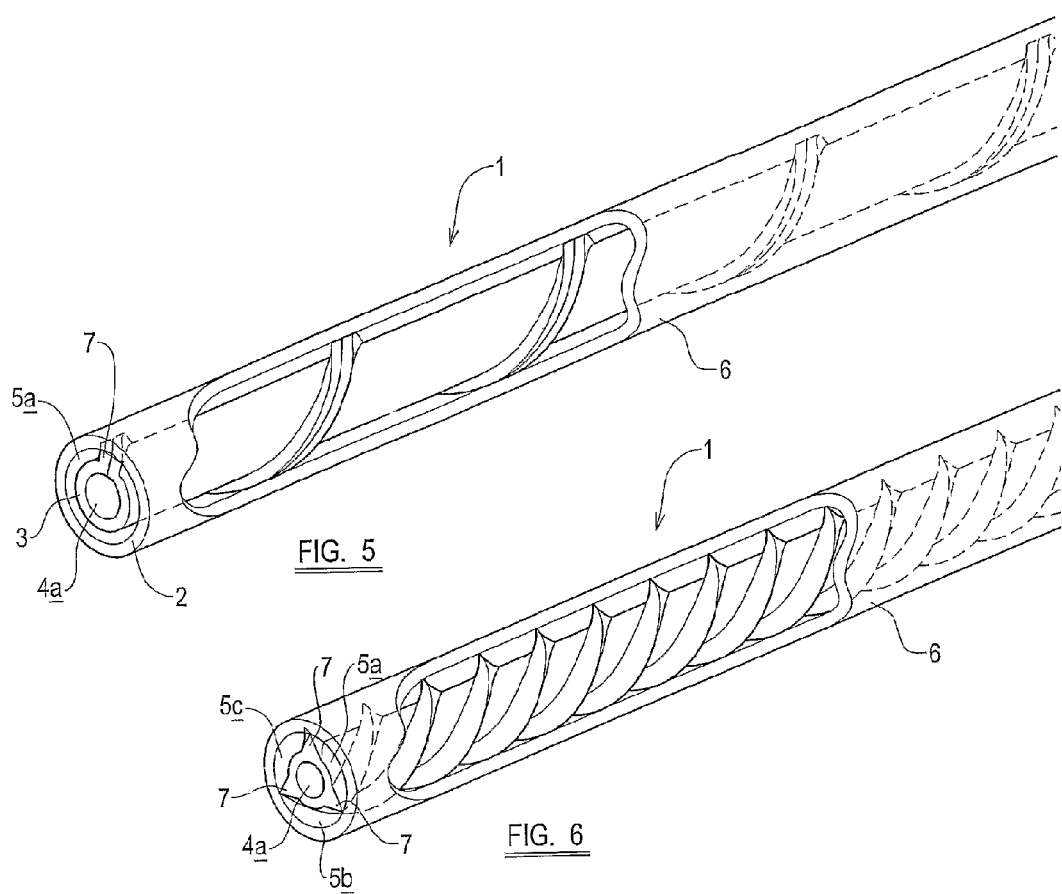

MOLECULAR EXCHANGE DEVICE

CROSS REFERENCE TO RELATED APPLICATIONS

This is the U.S. National Stage of International Application No. PCT/GB2009/000321 filed Feb. 5, 2009, published in English under PCT Article 21(2), which claims the benefit of Great Britain Application No. 0802667.6, filed Feb. 13, 2008, which is herein incorporated by reference in its entirety.

The present invention relates to a molecular exchange device. In particular, the present invention relates to a molecular exchange device for use in monitoring and delivering compounds.

Molecular exchange devices, such as dialysis probes, are known in the art. Such probes relate to use for insertion into a subject, such as in a blood vessel, for use in dialysis, detection of substances or levels of substances within the subject. Such probes generally include a porous membrane past which a perfusion fluid is supplied and removed. Molecules from the perfusion fluid can pass through the membrane into the subject and vice versa. In the latter case, analysis can be carried out using internal or external apparatus to ascertain the presence of certain molecules and their concentrations. Moreover such devices can be used to deliver substances, such as drugs, into a subject.

Known molecular exchange devices, as disclosed in U.S. Pat. No. 5,106,365 and US 2005119588, are provided with a outer tube having a lumen with a circular cross-section and an intra-luminal tube also having a circular cross-section positioned centrally within the outer tube, forming what is often referred to as a "concentric" arrangement defining an inner and an outer fluid passageway. The outer tube having a permeable membrane across which molecular exchange can take place. In such an arrangement perfusate fluid may be passed into and along one fluid passageway and drawn along and out of the other fluid passageway.

In order to increase efficiency of such probes; attempts have been made to optimise molecular exchange relative to the perfusate fluid volume and the molecular exchange surface area.

One approach to improve molecular exchange efficiency is to increase the length of the probe. However, such a probe is more clinically invasive and potentially increases the trauma caused by the insertion/removal of the probe to/from a subject. Moreover, when the probe is being used to sample/analyse perfusate fluid or to deliver drugs/other chemicals for clinical purposes, the increase in the length of the probe creates a longer response time, thereby delaying the analysis of the extracted fluid which may have potential clinical implications and may also miss the relevant tissue for sampling if the functional portion is too long.

An alternative approach is to reduce the perfusate fluid flow rate in order to provide more time for absorption/desorption of analytes across the molecular exchange surface. Again this approach has the undesired effect of increasing the response time that may reduce the clinical usefulness of such a probe.

Another known approach to improve the exchange efficiency of a probe was to provide two fluid passageways side by side, rather than in the concentric arrangement. Although this provides an efficient molecular exchange, the arrangement increases the overall diameter of the probe and, as such, increases the damage caused by the insertion/removal of the probe to/from a subject.

Under the pressure of fluid flow the originally centrally positioned inner tube does not remain concentric with respect to the outer tube, but is displaced laterally. This displacement may lead to distortion of the cross-section of the outer tube and may also lead to the inner tube resting against the inside of the hollow tube as shown in Bungay Abstract, Proceedings of the $3^{rd}$ International Symposium on Microdialysis in Research and Development, Minneapolis. Minn., USA, June 2002, Poster E). Furthermore, it is often difficult to manufacture a probe having the desired concentric arrangement due to difficulties during manufacture caused by the small size of microdialysis probes. In light of these difficulties the resulting probes often have an inner tube positioned in at least a slightly eccentric position within the outer tube. Moreover, the lateral position of the inner tube may be displaced during use, such as during insertion of the probe into a subject. The lateral displacement of the inner tube reduces extraction efficiency of a probe and can significantly contribute to variability of extraction efficiency of a probe.

It is an object of the present invention to provide a molecular exchange device that has overcomes or mitigates some or all of the above disadvantages.

In a first aspect of the present invention there is provided a molecular exchange device comprising an outer tube extending from a proximal end to a distal end of the device; an inner tube defining at least one fluid passageway, the inner tube positioned concentrically, within the outer tube and the area between the inner and the outer tube defining at least one fluid pathway; and a projection positioned within the area between the inner and the outer tube, wherein the projection prevents displacement of the inner tube with respect to the outer tube. Molecular exchange occurs across a porous region in the outer membrane.

The main advantage provided by the molecular exchange device in accordance with the present invention is that the maintenance of the inner tube in a concentric position with regard to the outer tube enhances the extraction efficiency of the device, by increasing the absorption/desorption of analytes in perfusate fluid and/or increasing the uniformity of distribution of the analyte of interest throughout the fluid passageways.

In a preferred embodiment, the projection extends from the outer tube and/or the inner tube. In an advantageous environment, the projection extends from the inner tube.

In an advantageous embodiment of the invention the projection is integral with the outer and/or inner tube. For example, the inner tube and the projection may be formed as a single extrusion.

In an embodiment of the invention, the projection is positioned along the outer and/or inner tube at the distal and/or proximal end of the device. In a preferred embodiment of the invention, the projection extends along substantially the entire length of the outer and/or inner tube. Such arrangements ensure that the concentric position of the inner tube relative to the outer tube is maintained.

In an advantageous embodiment the projection extends continuously along the length of outer and/or inner tube. In such an embodiment, the projection may extend continuously along a part of the length of the outer and/or inner tube or substantially the entire length of the outer and/or inner tube. In an alternative embodiment, the projection extends discontinuously along the length of the outer and/or inner tube. Again, the projection may extend discontinuously along a part of the length of the outer and/or inner tube or along substantially the full length of the outer and/or inner tube.

In a preferred embodiment, the projection is a single protrusion extending radially from the inner tube. Alternatively, the projection is a single protrusion extending from the outer tube.

In an advantageous embodiment, the projection is two or more protrusions each extending radially from the inner tube. Alternatively, the two or more projections each extend from the outer tube. The two or more projections may extend from the outer and/or inner tubes'. Advantageously, the two or more protrusions define two or more separate fluid passageways in the area between the outer tube and inner tube. The separate fluid passageways may be used for different functions, such as carrying fluids or probes for recording measurements, ascertaining the position of the device and/or analysis. Such probes may be in the form of a fibre or wire.

Advantageously the one or more protrusions are positioned around the outer or inner tube in a spiral arrangement. This arrangement provides a secondary fluid pathway within the fluid passageways, which increases the uniformity of distribution of analyte(s) in the perfusion fluid and subsequently improves the absorption/desorption of analyte(s) into/from the perfusion fluid that passes along the fluid passageways. This arrangement also increases the area for molecular exchange without increasing the length of the device.

In the embodiment of the invention wherein the projection is positioned along the outer and/or inner tube at the distal and/or proximal end of the device, preferably, the projection is a porous mesh positioned around the circumference of the inner tube.

In a preferred embodiment the projection is in the form of a plurality of protuberants. When perfusate fluid flows over a plurality of protuberants local-mixing occurs at each protuberant, which increases the uniformity of distribution of analyte(s) in the perfusion fluid and subsequently improves the absorption/desorption of analyte(s) into/from the perfusion fluid that passes along the fluid passageways. Advantageously, the protuberants are positioned in a uniform manner around the circumference of the inner tube, in order to improve the uniformity of the distribution of analyte(s) in the perfusate fluid. Alternatively, the plurality of protuberants are positioned in a spiral arrangement around the circumference of the inner tube or in a spiral arrangement around the internal circumference of the outer tube. This arrangement provides a secondary fluid pathway within the fluid passageways, which increases the uniformity of distribution of analyte(s) in the perfusion fluid and subsequently improves the absorption/desorption of analyte(s) into/from the perfusion fluid that passes along the fluid passageways.

In an alternative embodiment, the projection is in the form of a plurality of indentations. When perfusate fluid flows over a plurality of protuberants local-mixing occurs at each protuberant, which increases the uniformity of distribution of analyte(s) in the perfusion fluid and subsequently improves the absorption/desorption of analyte(s) into/from the perfusion fluid that passes along the fluid passageways. Advantageously, the protuberants are positioned in a uniform manner around the circumference of the inner tube, in order to improve the uniformity of the distribution of analyte(s) in the perfusate fluid.

In an advantageous embodiment, the molecular exchange device further comprises an impeller. As is the nature of impellers, this cause the fluid to flow through the fluid passageways in a circular/spiral arrangement that increases the uniformity of distribution of analyte(s) in the perfusion fluid and subsequently improves the absorption/desorption of analyte'(s) into/from the perfusion fluid that passes along the fluid passageways. Conveniently, the impeller is positioned within the outer tube. However, the impeller may be positioned outside of the outer tube, adjacent to the proximal end of the device.

The impeller may be in the form of a protrusion in the form of a spiral that provides a secondary pathway. Alternatively, the impeller may be in the form of a propeller that drives the fluid in a circular/spiral pathway. The propeller may be driven externally by a magnetic force.

In an advantageous embodiment, the inner tube defines a plurality of fluid passageways. As discussed above with regard to the fluid passageways provided in the area between the outer tube and inner tube, the separate fluid passageways may be used for different functions, such as carrying fluids or probes for recording measurements, ascertaining the position of the device and/or analysis. Such probes may be in the form of a fibre or wire.

The plurality of fluid passageways defined by the inner tube may have a fluid relationship with one or more of the fluid passageways provided in the area between the outer tube and the inner tube.

In a preferred embodiment, the outer tube is a porous membrane enabling molecular exchange to occur across any part of the outer tubing that comes into contact with the external environment of a subject. Advantageously, the outer tube is a dialysis membrane. In an alternative embodiment the outer tubing has one or more porous areas where molecular exchange may occur. In embodiments having more than one porous area the porous areas have different porosities. The porosity of each porous area will depend upon the intended function of the fluid pathway adjacent to the specific porous area.

Preferably, the molecular exchange device further comprises a casing. The casing supports and protects the outer tube.

Advantageously, the proximal end of the device is adapted for attachment to a catheter and/or cannular. More advantageously, the proximal end of the device is a lockable-mating arrangement and or anchoring member for connecting to an invasive port. Conveniently, the proximal end of the device is adapted for attachment to a pump. Preferably, the proximal end of the device is adapted for attachment to an external device.

Advantageously, the device further comprises a sensor arrangement to, preferably, enable spectrologic measurement. More preferably, the spectrologic measurement is spectrophotometric measurement. Conveniently, the sensor arrangement is a reflector, wave guide, conductor, photoelectric, electro-active or electrochemical sensor.

For the avoidance of doubt, the following terms are intended to have the definitions as outlined below:

Molecular exchange is the selective exchange of any suitable molecule or composition, including but not limited to dialysis, ultra filtration, drug delivery etc. The selective exchange may be transfer of such suitable molecule or composition from the device to the external environment, transfer of such suitable molecule or composition from the external environment to the device or both.

The distal end of the device is the end of the device that can be inserted into the environment in which molecular exchange is desired.

The proximal end of the device is the end of the device that is not intended to be inserted into the environment in which molecular exchange is desired.

The distal and proximal ends of the device are adapted to allow the insertion/withdrawal of perfusion fluid to/from the fluid passageways.

The distal and proximal ends are also adapted to allow insertion/withdrawal of additional components, such as probes, sensors, connectors to monitoring/analysing systems etc.

The extraction efficiency of a molecular exchange device depends on the ability of the device to effectively absorb/desorb compounds of interest in the fluid passageways across the porous area of the outer tube.

The outer tube is a hollow cylinder having a substantially circular cross-section. Preferably, the cylinder is elongated.

The inner tube is a hollow cylinder defining at least one fluid passageway. Preferably, the cylinder is elongated. The inner tube is positioned centrally within the outer tube such that the inner and outer tubes share a common central axis, i.e. are in a concentric arrangement.

Preferably, the cross section of at least part of the inner tube is configured to maintain the inner tube in a concentric position within the outer tube, i.e. to prevent lateral displacement of the inner tube from the central position to a eccentric position within the outer tube. The cross-section of the inner tube can be any shape that maintains the position of the inner tube with respect to the outer tube.

The projections may be any shape. The projection may be one or more protrusions or a plurality of protuberants. The protrusions may be any shape and extend radially away from the inner tube. The protuberants may be any shape.

The porous area permits the exchange of selected molecules to/from the fluid passageway from/to the environment external to the device. The porous areas are porous to the extent that they permit the selective exchange of molecules across the fluid passageway and/or casing. A skilled person would appreciate that different sized molecules will require different porosities to permit the selective exchange of molecules.

The subject is any suitable environment in which the device may be applied. For example, the subject can be a human or animal body. Alternatively, the subject could be a vessel that is part of an industrial, chemical or fermentation process.

In order that the present invention may be more readily understood, non limiting embodiments thereof will now be described, by way of example, with reference to the accompanying drawings in which:

FIG. 5 is an alternative embodiment of a molecular exchange device in accordance with the present invention;

FIG. 6 is an alternative embodiment of a molecular exchange device in accordance with the present invention;

Figure 1:
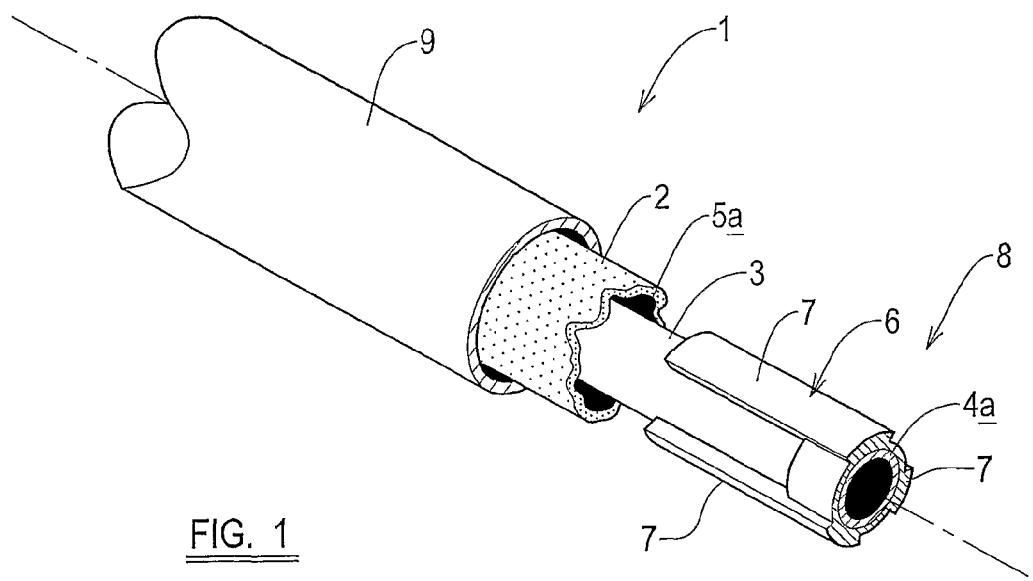
FIG. 1 is a cut away view of a first embodiment of a molecular exchange device in accordance with the present invention.

As illustrated in FIG. 1, there is a first embodiment of a molecular exchange device (1) according to the present invention comprising an outer tube (2) and an inner tube (3), the inner tube (3) defining a fluid passageway (4a). The inner tube (3) is positioned concentrically within the outer tube (2). The area between the outer tube (2) and the inner tube (3) defining a fluid passageway (5a). The fluid passageways (4a, 5a) are suitable for fluid to travel within the passageway. The fluid may be supplied to or drawn from the fluid passageways (4a, 5a).

In this embodiment, the outer tube (2) is in the form of a porous membrane that allows selective molecular exchange of molecules in one or both directions across the membrane. The level of porosity of the porous membrane will depend upon the intended use of the molecular device (1). The porosity enables a specific molecule or composition to cross the membrane from the environment external to the outer tube (2) and vice versa, for a particular use of the molecular exchange device (1). A casing (9) is provided around the outer tube (2) in the areas in which molecular exchange is not desired. The casing may be in any form that prevents molecular exchange, such as a sheath or coating.

In this embodiment, the projection (6) is positioned at the distal end of the device (8), within the area between the outer tube (2) and the inner tube (3) that prevents the lateral displacement of the inner tube (3) with respect to the outer tube (2). The projection (6) is positioned around the circumference of the inner tube (3), having three protrusions (7) extending from and partially along the length of the inner tube (3). In this embodiment the projection (6) is not integral with the inner tube (3). The projection (6) may be bonded to the inner tube, such as by an adhesive, or treated in such a way to shrink-fit onto the inner tube (3).

Figure 2:
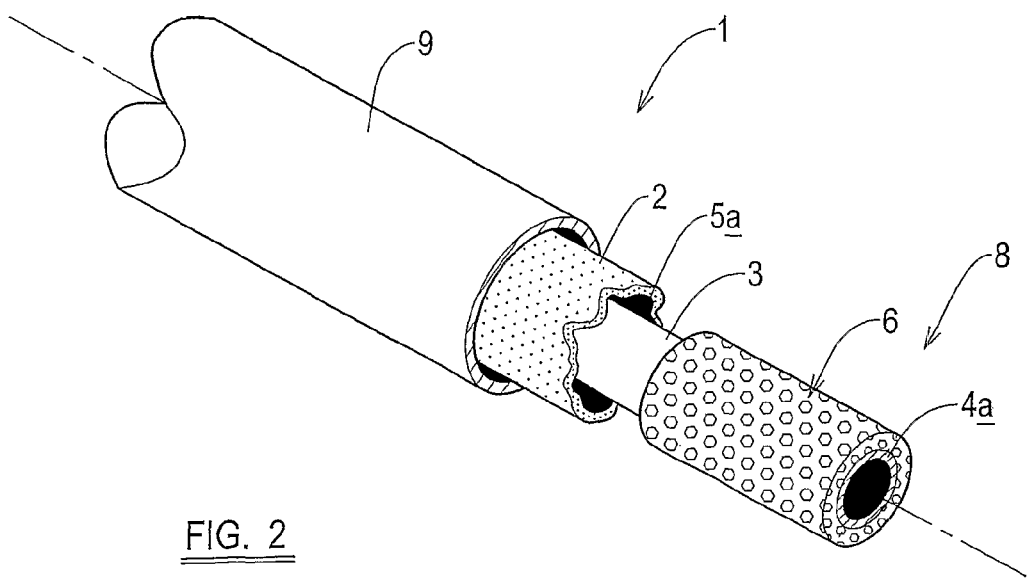
FIG. 2 is a cut away view of an alternative embodiment of a molecular exchange device in accordance with the present invention.

In an alternative embodiment, shown in FIG. 2, the projection (6) is positioned at the distal end (8) of the device (1), in the form of a porous mesh/matrix. The porous mesh/matrix prevents the lateral displacement of the inner tube (3) with respect to the outer tube (2) and enables perfusion fluid to pass there through. The projection (6) may be bonded to the inner tube, such as by an adhesive, or treated in such a way to shrink-fit onto the inner tube (3).

Figure 3:
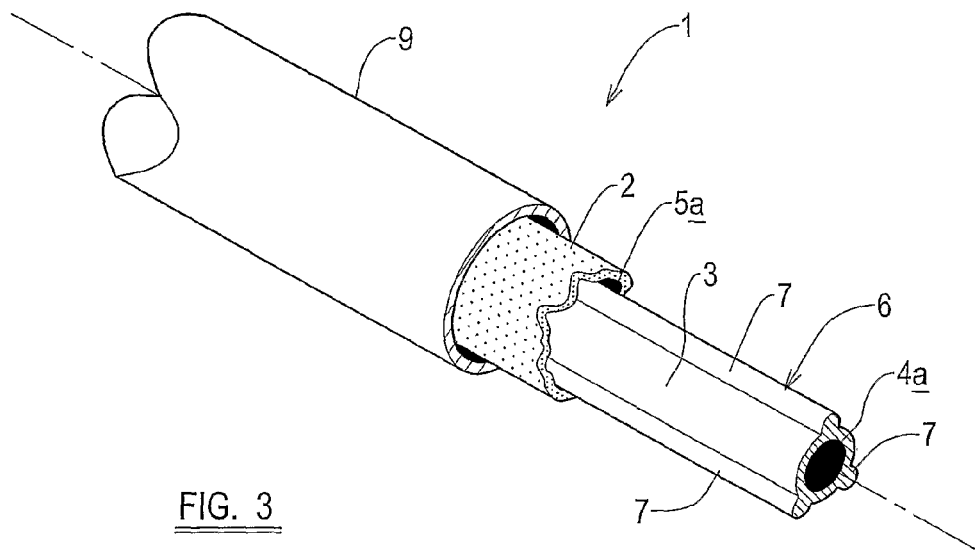
FIG. 3 is a cut away view of an alternative embodiment of a molecular exchange device in accordance with the present invention.
Figures 4A, 4B, 4C, 4D:
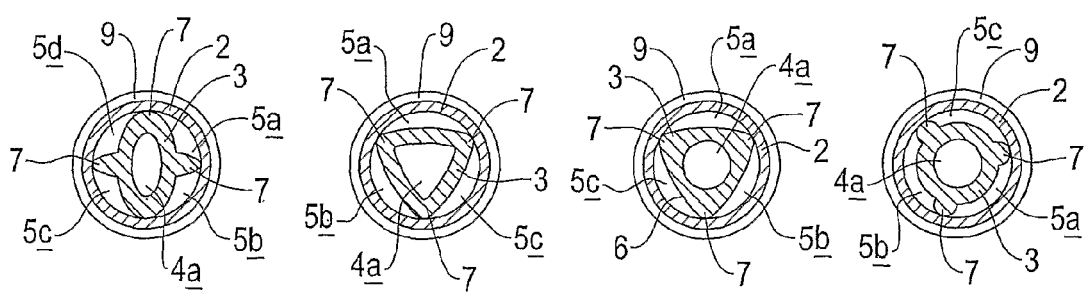
FIGS. 4a to 4d are cross-sectional views of alternative embodiments of a molecular exchange device in accordance with the present invention.

In a further embodiment illustrated in FIG. 3, the projection (6) is in form of three protrusions (7) positioned within the area between the outer tube (2) and the inner tube (3), which prevents displacement of the inner tube (3) with respect to the outer tube (2). In this embodiment, the three protrusions (7) extend from, and are integral with, the inner tube (3). The projection (6), in the form of the three protrusions (7), extends continuously along substantially the entire length of the inner tube (3).

As shown in FIGS. 4a, 4b, 4c and 4d, the projections (6) may have any form or shape that enables them to carry out the function of preventing displacement of the inner tube (3) with respect to the outer tube (2).

Also as shown in FIGS. 4a, 4b, 4c and 4d, the projections define multiple separate fluid passageways (5a, 5b, 5c, 5d) in the area between the outer and inner tubes (2, 3). The fluid passageways (5a) may have the same properties (for example porosity) as the other fluid passageways (5b, 5c 5d) and used for the same function. Alternatively, the separate fluid passageways (5a, 5b, 5c, 5d) could be used to supply and/or absorb different molecules/compositions and, as such, have different properties to one another.

FIGS. 5 and 6 illustrate embodiments in which the projection (6) is positioned around the inner tube (3) in a spiral arrangement. In each of the embodiments of FIGS. 5 and 6, the projection integral with the inner tube (3) and extends continuously along substantially the full length of the inner tube (3). In FIG. 5 the projection is on the form of one protrusion (8) extending radially from the inner tube (3), which defines one fluid passageway (4b). In FIG. 6 the projection is on the form of three protrusions (8) extending radially from the inner tube (3), which define three fluid passageways (4b).

This spiral arrangement for the fluid passageways (5a, 5b, 5c) provides a secondary fluid pathway within each of the fluid passageways (5a, 5b, 5c), which increases the uniformity of distribution of analyte(s) in the perfusion fluid and subsequently improves the absorption/desorption of analyte(s) into/from the perfusion fluid that passes along the fluid passageways (5a, 5b, 5c).

Figure 7:
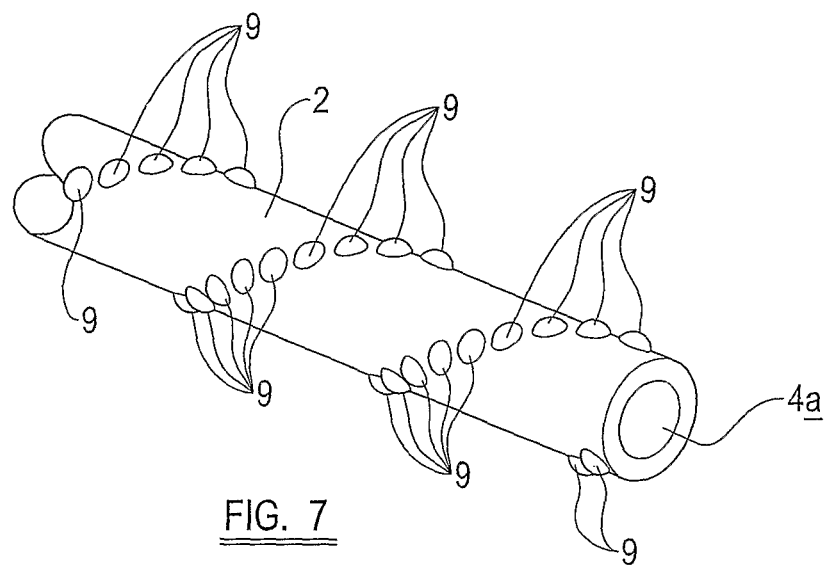
FIG. 7 is an alternative embodiment of an inner tube and projection of a molecular exchange device in accordance with present invention.

In an alternative embodiment, the projection (6) is in the form of a plurality of protuberants (9) positioned in a uniform manner around the circumference of the inner tube (2), as illustrated in FIG. 7. In use, when perfusate fluid passes along the fluid passageways (5a) and flows over the plurality of protuberants (9), local-mixing occurs at each protuberant (9).

Figure 8:
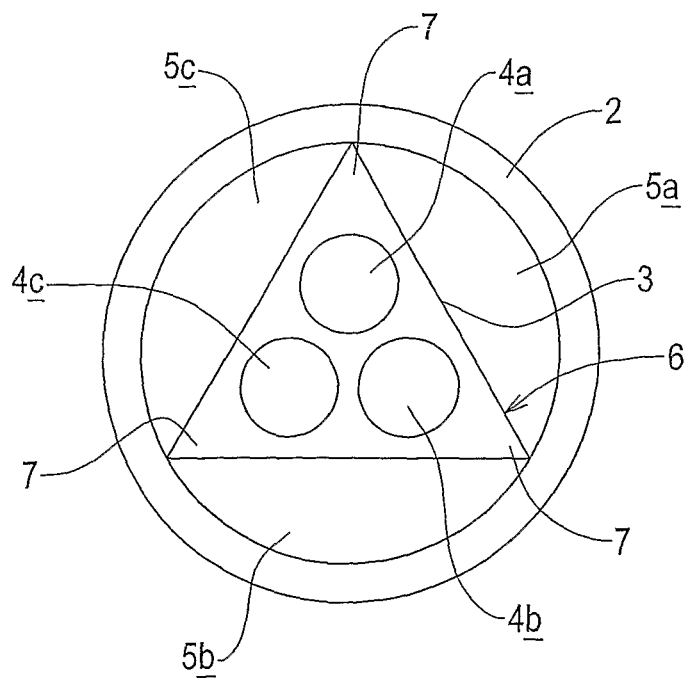
FIG. 8 is a cross-section view of an alternative embodiment of a molecular exchange device in accordance with the present invention.

As illustrated in FIG. 8, in a further embodiment the molecular exchange device comprises an inner tube (3) defining three fluid passageways (4a, 4b, 4c). The inner tube (3) has three protrusions (7), extending continuously along substantially the entire length thereof, that defines three separate fluid passageways (5a, 5b, 5c) in the area between the outer tube (2) and inner tube (3). Each one of the fluid passageways (4a, 4b, 4c) is in fluid communication with a respective fluid passageway (5a, 5b, 5c).

In use, it is envisaged that each set of respective fluid passageways (4a: 5a, 4b: 5b, 4c: 5c) will be suitable for different functions. For example, fluid may be passed along a first fluid passageway (4a), from the proximal end to the distal end of the device (1). The fluid is then passed from the distal end to the proximal end of the device along a respective first fluid passageway (5a). As the fluid passes along the respective fluid passageway (5a), the fluid is exposed to the external environments at porous areas of the outer tube (2), permitting the selective exchange of molecules/compositions across the porous area. Such a first set of fluid passageways (4a, 5a) is used to analyse the concentration of a specific analyte in the external environment in which the device (1) has been placed. Fluid may be passed in a similar manner along a second set of respective fluid passageways (4b, 5b). The second set of fluid passageways (4b, 5b) delivers a drug into the external environment in an amount dependent on the analysis of the first fluid passageway. The third set of fluid passageways (4c, 5c) carries a probe monitoring the position of the device (1) in the subject.

It is to be appreciated that the form of projection for a specific device will depend upon the intended function of the device. The physical parameters of the analyte and perfusate fluid (for example, density, viscosity, concentration, diffusivity), flow rates, response time and size of the inner and outer tubes will determine which form of projection is most efficient for a specific use.

The molecular exchange device of the present invention and one or more external devices can be used to analyse, measure or deliver industrial, chemical, fermentation and animal or plant compositions. The molecular exchange device may be used in a vessel of industrial, chemical or fermentation processes and the human or animal body.

The molecular exchange device according to the present invention is intended to be used in the human or animal bodies in any tissue or organ including but not restricted to the circulatory system, insertion into blood vessels, lymphatic system, muscles, ear, mouth, tissue fat and internal organs.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A molecular exchange device comprising:
   an outer tube extending from a proximal end to a distal end of the device;
   an inner tube defining at least one fluid passageway, the inner tube positioned concentrically within the outer tube and the area between the inner and the outer tube defining at least one fluid passageway; and
   a projection positioned within the area between the inner and the outer tube, wherein the projection prevents displacement of the inner tube with respect to the outer tube;
   wherein at least a portion of the outer tube comprises a porous membrane that allows molecules in an external fluid to migrate across the porous membrane into the fluid passageway between the inner and outer tubes and molecules in a fluid within the fluid passageway between the inner and outer tubes to migrate across the porous membrane into an external fluid;
   wherein the inner tube has a circumference and the projection is a porous mesh positioned around the circumference of the inner tube;
   wherein the projection extends from the inner tube.

2. A molecular exchange device according to claim 1, wherein the projection extends from the outer tube and the inner tube.

3. A molecular exchange device according to claim 1, wherein the projection is integral with the outer tube or the inner tube.

4. A molecular exchange device according to claim 1, wherein the projection is positioned at the distal end or the proximal end of the device.

5. A molecular exchange device according to claim 1, further comprising an impeller.

6. A molecular exchange device according to claim 5, wherein the impeller is positioned within the outer tube.

7. A molecular exchange device according to claim 1, wherein the inner tube defines a plurality of fluid passageways.

8. A molecular exchange device according to claim 1, wherein the outer tube is a porous membrane.

9. A molecular exchange device according to claim 8, wherein the outer tube is a dialysis membrane.

10. A molecular exchange device according to claim 1, further comprising a casing.

11. A molecular exchange device according to claim 1, wherein:
   the proximal end of the device is adapted for attachment to a catheter or a cannular.

12. A molecular exchange device according to claim 1, further comprising a sensor arrangement to enable spectrologic measurement.

13. A molecular exchange device according to claim 12, wherein the spectrologic measurement is spectrophotometric measurement.

14. A molecular exchange device according to claim 1, wherein:
   the proximal end of the device is a lockable-mating arrangement or an anchoring member for connecting to an invasive port.

15. A molecular exchange device according to claim 1, wherein:

the proximal end of the device is adapted for attachment to a pump.

16. A molecular exchange device according to claim 1, wherein:
the proximal end of the device is adapted for attachment to an external device.

17. A molecular exchange device according to claim 1, wherein the at least one fluid passageway defined by the inner tube is in fluid communication with the at least one fluid passageway defined between the inner tube and the outer tube.

\* \* \* \* \*